US008124653B2

(12) United States Patent
Matalon et al.

(10) Patent No.: US 8,124,653 B2
(45) Date of Patent: Feb. 28, 2012

(54) METHODS AND COMPOSITIONS FOR THE TREATMENT OF ATTENTION DEFICIT HYPERACTIVITY DISORDER AND HYPERPHENYLALANEMIA

(75) Inventors: Reuben Matalon, Houston, TX (US); Ofer Matalon, Hayward, CA (US)

(73) Assignee: The Board of Regents of The University of Texas System, Austin, TX (US)

( * ) Notice: Subject to any disclaimer, the term of this patent is extended or adjusted under 35 U.S.C. 154(b) by 1359 days.

(21) Appl. No.: 11/630,589

(22) PCT Filed: Jun. 25, 2005

(86) PCT No.: PCT/US2005/022866
§ 371 (c)(1),
(2), (4) Date: Feb. 7, 2007

(87) PCT Pub. No.: WO2006/004719
PCT Pub. Date: Jan. 12, 2006

(65) Prior Publication Data
US 2008/0146577 A1 Jun. 19, 2008

Related U.S. Application Data

(60) Provisional application No. 60/583,089, filed on Jun. 25, 2004, provisional application No. 60/589,710, filed on Jul. 21, 2004.

(51) Int. Cl.
*A01N 43/08* (2006.01)
*A01N 43/58* (2006.01)
*A01N 43/60* (2006.01)
*A01N 43/90* (2006.01)
*A61K 31/34* (2006.01)
*A61K 31/50* (2006.01)
*A61K 31/495* (2006.01)
*A61K 31/519* (2006.01)
*C07D 473/00* (2006.01)

(52) U.S. Cl. ........ 514/469; 424/468; 514/249; 514/470; 514/472; 544/260

(58) Field of Classification Search .................. None
See application file for complete search history.

(56) References Cited

U.S. PATENT DOCUMENTS

| 4,550,109 | A | 10/1985 | Folkers et al. |
| 4,595,752 | A | 6/1986 | Azuma et al. |
| 4,758,571 | A | 7/1988 | Curtius et al. |
| 4,774,244 | A | 9/1988 | Curtius et al. |
| 4,778,794 | A | 10/1988 | Naruse et al. |
| 5,102,666 | A | 4/1992 | Acharya |
| 5,606,020 | A | 2/1997 | Watanabe et al. |
| 5,676,972 | A | 10/1997 | Galiatsatos et al. |
| 6,306,428 | B1 | 10/2001 | Lehmann et al. |
| 6,319,520 | B1 | 11/2001 | Wuthrich et al. |
| 6,319,521 | B1 | 11/2001 | Randolph et al. |
| 6,326,027 | B1 | 12/2001 | Miller et al. |
| 6,335,029 | B1 | 1/2002 | Kamath et al. |
| 6,342,250 | B1 | 1/2002 | Masters |
| 6,355,270 | B1 | 3/2002 | Ferrari et al. |
| 6,355,272 | B1 | 3/2002 | Caramella et al. |
| 6,667,297 | B2 | 12/2003 | Tsai et al. |
| 7,517,908 | B2 * | 4/2009 | Krishnan et al. .............. 514/469 |

OTHER PUBLICATIONS

Hoshiga et al.; Journal of Pharmacology and Experimental Therapeutics; vol. 267, No. 2, pp. 971-978; 1993.*
U.S. Patent Documents—None.*
Non-Patent Documents—None.*
Aziz, et al.; "Tetrahydrobiopterin Metabolism in Senile Dementia of Alzheimer Type"; Journal of Neurology, Neurosurgery and Psychiatry, vol. 46, pp. 410-413; 1983.
Barford, et al.; "Tetrahydrobiopterin Metabolism in the Temporal Lobe of Patients Dying with Senile Dementia of Alzheimer Type"; Journal of Neurology, Neurosurgery and Psychiatry; vol. 47, pp. 736-738; 1984.
Beck, et al.; "Diagnostic and Therapeutic Aspects of Dihydrobiopterin Deficiency"; Acta Paediatr Scand; vol. 72, pp. 449-454; 1983.
Chace, et al.; "Use of Phenylalanine-to-Tyrosine Ratio Determined by Tandem Mass Spectrometry to Improve Newborn Screening for Phenylketonuria of Early Discharge Specimens Collected in the First 24 Hours"; Clinical Chemistry, vol. 44, #12, pp. 2405-2409; 1998.
Chen; et al.; "Biophysical Characterization of the Stability of the 150-Kilodalton Botulinum Toxin, the Nontoxic Component, and the 900-Kilodalton Botulinum Toxin Complex Species"; Infection and Immunity, vol. 66, No. 6, pp. 2420-2425; Jun. 1998.
Crameri, et al.; "DNA Shuffling of a Family of Genes from Diverse Species Accelerates Directed Evoluation"; Nature, vol. 391, pp. 288-291; Jan. 15, 1998.
Crameri, et al.; "Improved Green Fluorescent Protein by Molecular Evolution Using DNA Shuffling"; Nature Biotechnology, vol. 14, pp. 315-319; Mar. 14, 1996.
Crameri, et al.; "Molecular Evolution of an Arsenate Detoxification Pathway by DNA Shuffling"; Nature Biotechnology, vol. 15, pp. 436-438; May 15, 1997.
Curtius, et al.; "Endogenous Depression and Parkinson's Disease: Therapeutic Trials with Tetrahydrobiopterin"; Biochemical and Clinical Aspects of Pteridines—Cancer • Immunology • Metabolic Diseases; ; vol. 1, pp. 285-292; 1982.
Curtius, et al.; "Parkinson-Specific Motor and Mental Disorders, Role of the Pallidum: Pathophysiological, Biochemical, and Therapeutic Aspects "Therapeutic Efficacy of Tetrahydrobiopterin in Parkinson's Disease""; Advances in Neurology; vol. 40, pp. 463-466; 1984.

(Continued)

*Primary Examiner* — Robert A Wax
*Assistant Examiner* — Jeffrey T Palenik
(74) *Attorney, Agent, or Firm* — Landrum Intellectual Property

(57) ABSTRACT

Disclosed is a composition that includes a tetrahydrobiopterin in a controlled-release pharmaceutical preparation. Also disclosed is a method of treating a patient with phenylketonuria that includes administering, to the patient, a composition that contains tetrahydrobiopterin in a controlled-release pharmaceutical preparation. Also disclosed is a method of treating a patient with ADHD that includes administering a tetrahydropterin to the patient. Compositions for the treatment of ADHD are also described.

22 Claims, No Drawings

OTHER PUBLICATIONS

Curtius, et al.; "Successful Treatment of Depression with Tetrahydrobiopterin"; The Lancet, vol. 321, pp. 657-658; Mar. 1983.

Curtius, et al.; "Tetrahydrobiopterin: Efficacy in Endogenous Depression and Parkinson's Disease"; Journal of Neural Transmission, vol. 55, pp. 301-308; 1982.

Dr. Kure, et al.; "Tetrahydrobiopterin-Responsive Phenylalanine Hydroxylase Deficiency"; The Journal of Pediatrics, vol. 135, No. 3, pp. 375-378; Sep. 1999.

Erlandsen, et al.; "A Structural Hypothesis for $BH_4$ Responsiveness in Patients with Mild Forms of Hyperphenylalaninaemia and Phenylketonuria"; Journal of Inherited Metabolic Disease, vol. 24, pp. 213-230; 2001.

Erlandsen, et al.; "Crystal Structure and Site-Specific Mutagenesis of Pterin-Bound Human Phenylalanine Hydroxylase"; Biochemistry, vol. 39, No. 9, pp. 2208-2217; 2000.

Fernell, et al.; "Possible Effects of Tetrahydrobiopterin Treatment in Six Children with Autism—Clinical and Positron Emission Tomography Data: A Pilot Study"; Developmental Medicine & Child Neurology; vol. 39, pp. 313-318; 1997.

Hase, et al.; "A Case of Tetrahydrobiopterin Deficiency Due to a Defective Synthesis of Dihydrobiopterin"; Journal of Inherited Metabolic Disease, vol. 5, pp. 81-82; 1982.

Hoskins, et al.; "Enzymatic Control of Phenylalanine Intake in Phenylketonuria"; The Lancet, vol. 315, pp. 392-393; Feb. 23, 1980.

Kaufman, Ph.D., et al.; "Tetrahydropterin therapy for Hyperphenylalaninemia Caused by Defective Synthesis of Tetrahydrobiopterin"; Annals of Neurology, vol. 14, No. 3; Sep. 1983.

Kaufman, Ph.D., et al.; "Use of Tetrahydropterins in the Treatment of Hyperphenylalanimemia Due to Defective Synthesis of Tetrahydrobiopterin: Evidence that Peripherally Administered Tetrahydropterins Enter the Brain"; Pediatrics, vol. 70, No. 3, pp. 376-380; Sep. 1982.

Leeming, et al.; "Intestinal Absorption of Tetrahydrobiopterin and Bopterin in Man"; Biochemical Medicine, vol. 30, pp. 328-332; 1983.

Leupold, et al.; "Tetrahydrobiopterin Monotherapy in Two Siblings with Dihydro-Biopterin Deficiency"; Biochemical and Clinical Aspects of Pteridines—Cancer • Immunology • Metabolic Diseases; vol. 1, pp. 307-317; 1982.

Massey, et al.; "Flavin and Pteridine Monooxygenases"; The Enzymes; vol. XII—Oxidation-Reduction, Part B; Third Edition; Chapter 4, pp. 191-252; 1975.

Matalon, et al.; "Screening for Biopterin Defects in Newborns with Phenylketonuria and Other Hyperphenylalaninemias"; Annals of Clinical and Laboratory Scienct; vol. 12, No. 5, pp. 411-414; 1982.

Moore, et al.; "Biopterin in Parkinson's Disease"; Journal of Neurology, Neurosurgery and Psychiatry; vol. 50, pp. 85-87; 1987.

Nagatsu, et al.; "Biosynthesis of Tetrahydrobiopterin in Parkinsonian Human Brain"; Advances in Neurology; vol. 45, pp. 223-226; 1986.

Narabayashi, et al.; "Tetrahydrobiopterin Adminstration for Parkinsonian Symptoms"; Proc. Japan Acad., 58, Ser. B, No. 9], pp. 283-287; 1982.

Niederwieser, et al.; Atypical Phenylketonuria with Defective Biopterin Metabolism. Monotherapy with Tetrahydrobiopterin or Sepiapterin, Screening and Study of Biosynthesis in Man; European Journal of Pediatrics, vol. 138, pp. 110-112; 1982.

Niederwieser, et al.; "GTP Cyclohydrolase I Deficiency, a New Enzyme Defect Causing Hyperphenylalaninemia with Neopterin, Biopterin, Dopamine, and Serotonin Deficiencies and Muscular Hypotonia"; European Journal of Pediatrics, vol. 141, pp. 208-214; 1984.

Sarkissian, et al.; "A Different Approach to Treatment of Phenylketonuria: Phenylalanine Degradation with Recombinant Phenylalanine Ammonia Lyase"; Proc. Natl. Acad. Sci, USA; vol. 96, pp. 2339-2344; Mar. 1999.

Schaub, et al.; "Tetrahydrobiopterin Therapy of Atypical Phenylketonuria Due to Defective Dihydrobiopterin Biosynthesis"; Archives of Disease in Childhood; vol. 53, pp. 674-683; 1978.

Spaapen, et al.; "Tetrahydrobiopterin-Responsive Phenylalanine Hydroxylase Deficiency in Dutch Neonates"; Journal of Inhterited Metabolic Disease, vol. 24, pp. 352-358; 2001.

Tani, et al.; "Decrease in 6R-5,6,7,8-Tetrahydrobiopterin Content in Cerebrospinal Fluid of Autistic Patients"; Neuroscience Letters, vol. 181, pp. 169-172; 1994.

Trefz, et al.; "Successful Treatment of Phenylketonuria with Tetrahydrobiopterin"; European Journal of Pediatrics; vol. 260, No. 5, p. 315; 2001.

Wei, et al.; "Tetrahydrobiopterin Radical Enzymology"; Chemical Reviewers, vol. 103, No. 6, pp. 2365-2383; 2003.

Yamaguchi, et al.; Effects of Tyrosine Administration on Serum Biopterin in Normal Controls and Patients with Parkinson's Disease; Science, vol. 219, Jan. 7, 1983; pp. 75-77.

Yano, et al.; "Directed Evolution of an Aspartate Aminotransferase with New Substrate Specificities"; Proc. Natl. Acad. Sci., USA; vol. 95, pp. 5511-5515; May 1998.

Zhang, et al.; "Directed Evolution of a Fucosidase from a Galactosidase by DNA Shuffling and Screening"; Proc. Natl. Acad Sci.; USA; vol. 94, pp. 4504-4509; Apr. 1997.

* cited by examiner

METHODS AND COMPOSITIONS FOR THE TREATMENT OF ATTENTION DEFICIT HYPERACTIVITY DISORDER AND HYPERPHENYLALANEMIA

The present application is the national stage entry of PCT/US2005/022866, filed Jun. 25, 2005, which claims the benefit of U.S. Provisional Patent Application Ser. No. 60/583,089, filed Jun. 25, 2004, and U.S. Provisional Patent Application Ser. No. 60/589,710, filed Jul. 21, 2004, each of which provisional patent applications is hereby incorporated by reference.

The present invention was made with the support of the National Institutes of Health, Grant No. 40898-01. The Federal Government may have certain rights in this invention.

FIELD OF THE INVENTION

The subject invention is directed, generally, to methods and compositions for the treatment of attention deficit hyperactivity disorder and hyperphenylalanemia and, more particularly, to the use of tetrahydrobiopterins in methods and compositions for the treatment of attention deficit hyperactivity disorder and to methods and compositions for the treatment of hyperphenylalanemia using a controlled, sustained, or time-release formulation of tetrahydrobiopterin.

BACKGROUND OF THE INVENTION

Tetrahydrobiopterin

Tetrahydrobiopterin ("BH4") is a co-factor for the enzymes phenylalanine hydroxylase, tyrosine hydroxylase and tryptophan hydroxylase. The 6R-stereoisomer is believed to be the active form of the BH4 co-factor. The tyrosine hydroxylase and tryptophan hydroxylase enzymes are rate-limiting enzymes in the biosynthesis of neurotransmitters such as dopamine and serotonin. BH4 is considered to be a regulating factor in the biosynthesis of these neurotransmitter amines since BH4 is contained in nerve endings only in an amount which is approximately the Km value of each hydroxylase; a shortage or decrease in enzymes which participate in the biosynthesis of this co-factor from GTP is known to give rise to a decrease in neurotransmitter amines, thus resulting in various neuropsychiatric diseases; researchers (U.S. Pat. No. 5,606,020 to Watanabe et al., which is hereby incorporated by reference) demonstrated that 6R-BH4 enhances the release and liberation of neurotransmitter amines such as dopamine ("DA"), norepinephrine, and serotonin, and that it also enhances the liberation of glutamic acid, aspartic acid or gamma-aminobutyric acid ("GABA") via DA and the release of acetylcholine via serotonin. On the other hand, it has also been also demonstrated that, when the endogenous BH4 level is lowered by inhibiting the biosynthesis of BH4, the DA level per se is not significantly changed, whereas the release of DA is suppressed by 50-fold or lower. The latter findings suggested that the endogenous BH4 triggers some change in the mechanism of DA release.

Further research (U.S. Pat. No. 5,606,020 to Watanabe et al., which is hereby incorporated by reference) into the molecular mechanism of DA release, isolated, in a membrane fraction of the brain, a receptor site saturated by 6R-BH4 which had both high affinity and high specificity for BH4 and which is the possible regulatory site in the DA release mechanism. It was further found that, because of said specificity, the 6R-BH4 receptor is capable of strictly distinguishing 6R- and 6S-optical isomers of tetrahydrobiopterin and, thus, is capable of selectively recognizing the 6R-isomer, believed to be the active form of the co-factor.

Studies of phenylketonuria have implicated either deficiency in the enzyme phenylalanine hydroxylase (classical PKU) and/or a deficiency in its BH4 co-factor (atypical PKU) as causative agents of this disease (Schaub et al., "Tetrahydrobiopterin Therapy of Atypical Phenylketonuria Due to Defective Dihydrobiopterin Biosynthesis," Arch. Dis. Child., 53(8):674-676 (1978); Matalon et al., "Screening for Biopterin Defects in Newborns with Phenylketonuria and Other Hyperphenylalaninemias," Ann. Clin. Lab. Sci., 12(5):411-414 (1982); Kaufman et al., "Use of Tetrahydropterins in the Treatment of Hyperphenylalaninemia Due to Defective Synthesis of Tetrahydrobiopterin: Evidence That Peripherally Administered Tetrahydropterins Enter the Brain," Pediatrics, 70(3):376-380 (1982); which are hereby incorporated by reference). Autopsied brain specimens and cerebrospinal fluid of patients with Parkinson's disease (Moore et al., "Biopterin in Parkinson's Disease," J. Neurol. Neurosurg. Psychiatry, 50(1):85-87 (1987); Nagatsu et al., "Biosynthesis of Tetrahydrobiopterin in Parkinsonian Human Brain," Adv. Neurol., 45:223-226 (1987); which are hereby incorporated by reference), Alzheimer's dementia (Barford et al., "Tetrahydrobiopterin Metabolism in the Temporal Lobe of Patients Dying with Senile Dementia of Alzheimer Type," J. Neurol. Neurosurg. Psychiatry, 47(7):736-738 (1984), which is hereby incorporated by reference), and infantile autism (Tani et al., "Decrease in 6r-5,6,7,8-tetrahydrobiopterin Content in Cerebrospinal Fluid of Autistic Patients," Neurosci. Lett., 181 (1-2):169-172 (1994), which is hereby incorporated by reference) show a decrease in BH4 content. Supplementation therapy by BH4 has been studied on a small-scale and proposed for the treatment of phenylketonuria (see references cited above), Parkinson's disease (Curtius et al., "Therapeutic Efficacy of Tetrahydrobiopterin in Parkinson's Disease," Adv. Neurol., 40:463-466 (1984), which is hereby incorporated by reference), Alzheimer's disease (Aziz et al., "Tetrahydrobiopterin Metabolism in Senile Dementia of Alzheimer Type," J. Neurol. Neurosurg. Psychiatry, 46(5):410-413 (1983), which is hereby incorporated by reference), depression (Curtius et al., "Successful Treatment of Depression with Tetrahydrobiopterin," Lancet, 1(8325):657-658 (1983) and infantile autism (Fernell et al., "Possible Effects of Tetrahydrobiopterin Treatment in Six Children with Autism—Clinical and Positron Emission Tomography Data: A Pilot Study," Dev. Med. Child Neurol., 39(5):313-318 (1997), which is hereby incorporated by reference). Based on these proposals, as of 1997, over a hundred BH4 derivatives had been designed as drugs in Switzerland, the United States and Japan and screened for their co-factor action analogous to BH4. None of these derivatives had demonstrated activity superior to BH4 (U.S. Pat. No. 5,606,020 to Watanabe et al., which is hereby incorporated by reference).

Disappointment with the degree of therapeutic efficacy of BH4 was thought to be due to low penetration of the blood-brain barrier and it was thus suggested that the more lipophilic 6-methyl BH4 (Kaufman et al., "Tetrahydropterin Therapy for Hyperphenylalaninemia Caused by Defective Synthesis of Tetrahydrobiopterin," Ann. Neurol., 14(3):308-315 (1983), which is hereby incorporated by reference) should improve BH4 therapeutic efficacy by increasing penetration of the blood-brain barrier. Since BH4 is a cofactor needed to generate catecholamine and serotonin, it is possible to find a new use for it, unrelated to PKU or PKU variants.

Attention Deficit Hyperactivity Disorder

Attention deficit hyperactivity disorder ("ADHD") is a condition characterized by a decreased attention span, hyperactivity, and/or impulsiveness inappropriate for a certain age. Typically, young children have what are known as subtle neurological signs of immaturity. These are involuntary movements of one part of the body that occur while the child is making a voluntary movement of another part of the body. This is referred to as synkinesis, or overflow movements. These overflow movements disappear during normal development and are usually gone by the age of 10. However, in children with ADHD these overflow movements tend to be more intense and last long after the age of 10. This leads researchers to believe there is an abnormality in the maturation and development of the brain areas associated with motor activity in children with ADHD.

Transcranial Magnetic Stimulation ("TMS") is a non-invasive technique that gives information about brain function and is very useful when studying areas of the nervous system related to motor activity (motor cortex, corticospinal tract, and corpus callosum). A magnetic signal given from a special instrument held close to the patient's head stimulates a small area of the brain that controls a few muscles (for example, the muscles that control one finger). Doctors put electrodes (small pieces of metal taped to areas of the body) over the muscle to measure the electrical activity the muscle produces when it makes a movement. When the magnetic signal activates those muscles, the electrodes pick up and record the electrical activity of the movement that the muscles make in response to the magnetic signal. Researchers are currently studying normal children and those diagnosed with ADHD using TMS to find out if the clinical abnormalities of ADHD are associated with a delay or abnormality in maturation of areas of the nervous system responsible for motor activity (motor cortex and corticospinal tract).

Despite a complete understanding of the cause of ADHD, certain pharmacological agent have been found to be effective in controlling the condition. Specifically, ADHD has been treated with pharmacological agent that mimic catecholamine or serotonin (e.g., psychostimulants, such as methylphenidate (also referred to as RITALIN™)). A Phase III clinical trial is underway to evaluate the benefits and side effects of two medications, clonidine and methylphenidate, used either alone or in combination to treat ADHD in children. Current pharmacotherapeutics for ADHD are psychostimulants, such as RITALIN™; a time-released methylphenidate (CONCERTA™), marketed by McNeil Consumer and Specialty Pharmaceuticals Inc.; ADDERALL™ (an amphetamine), marketed by Richwood Pharmaceutical Co. Inc.; CYLERT™ (pemoline, 2-amino-5-phenyl-2-oxazolin-4-one); DESOXYN™ (methamphetamine), marketed by Abbott Laboratories; and the antihypertensive CATAPRES™ (clonidine, 2-(2,6-dichlorophenylimino)imidazolidine), marketed by Boehringer-Ingelheim.

There is a need for methods and compositions for treating ADHD, and the present invention, in part, is directed to addressing this need.

Hyperphenylalanemia

Hyperphenylalaninemia ("HPA") is the presence of elevated levels of phenylalanine in the blood, which may result in brain damage and other pathologies. HPA is typically caused by defect(s) in either the BH4 synthetic pathway or the phenylalanine metabolic pathway. The key enzyme in the phenylalanine metabolic pathway is the enzyme phenylalanine-4-hydroxylase ("PAH"). Defects in PAH result in the metabolic disorder Phenylketonuria ("PKU"), which is associated with HPA. Although progress in the neurosciences has been both rapid and broadly based, it has offered little to the practicing pediatrician in regard to treatment of HPA.

Phenylketonuria is a metabolic disease caused by a defect in the activity of PAH, which converts phenylalanine to tyrosine. Accumulation of phenylalanine and its neurotoxic metabolites can produce brain damage in PKU patients, resulting in mental retardation. There are approximately 400 known mutations of PAH resulting in syndromes of varying severity. In approximately 1% of cases, the defect in PAH activity is due to mutation in genes encoding the enzymes such as dihydropteridine reductase ("DHPR"), which are involved in production of the required cofactor (BH4) of PAH.

Although a diet low in phenylalanine can ameliorate the severe retardation associated with untreated PKU, dietary compliance becomes problematic as PKU patients reach adolescence, leading to a rise in phenylalanine blood levels and a loss of intelligence and white matter changes in the brain. Nutritional deficiencies may result from phenylalanine restricted diets, which are typically designed to achieve a safe phenylalanine blood level, which is in the approximate range of 2-6 mg/dL. Furthermore, PKU females of child-bearing age are candidates to have children with Maternal PKU syndrome, characterized by microcephaly, mental retardation and serious congenital heart defects. Investigations into more convenient modes of PKU treatment, other than diet, are needed.

In 1980, Hoskins et al., "Enzymatic Control of Phenylalanine Intake in Phenylketonuria," *Lancet*, 1(8165):392-394 (1980), which is hereby incorporated by reference, proposed treatment of PKU via administration of phenylalanine ammonia lyase ("PAL"), a yeast-produced enzyme which converts phenylalanine to cinnamic acid and ammonia, and which, unlike PAH, does not require cofactors. However, limited studies on humans indicated a variable and unpredictable response and the treatment was not cost-effective. Research into PAL therapy was revived in Sarkissian et al., "A Different Approach to Treatment of Phenylketonuria: Phenylalanine Degradation with Recombinant Phenylalanine Ammonia Lyase," *Proc. Natl. Acad. Sci., USA.*, 96(5):2339-2344 (1999), where it was demonstrated that recombinant PAL lowered blood phenylalanine levels in PKU knockout mice having no PAH activity.

An additional therapeutic regimen for PKU is BH4 loading in patients with residual or low PAH activity or defective BH4 synthesis. Kure et al., "Tetrahydrobiopterin-Responsive Phenylalanine Hydroxylase Deficiency," *J. Pediatr.*, 135(3):375-378 (1999), which is hereby incorporated by reference, reported a successful response of four PKU patients to oral administration of the BH4 cofactor. Also, Trefz et al., "Successful Treatment of Phenylketonuria with Tetrahydrobiopterin," *Eur. J. Pediatr.*, 160(5):315 (2001) and Spaapen et al., Tetrahydrobiopterin-Responsive Phenylalanine Hydroxylase Deficiency in Dutch Neonates," *J. Inherit. Metab. Dis.*, 24(3): 352-358 (2001), which are hereby incorporated by reference, have reported similar success with one and five PKU patients in Germany and the Netherlands, respectively. All PKU patients in these studies had normal levels of BH4 prior to treatment, were double heterozygous for PKU mutations with one mutation considered "atypical" (where "atypical", in this context refers to a phenylalanine level in blood of 6-20 mg/dL)) and responded to BH4 oral administration with normalization of blood levels of phenylalanine, without the need of a low phenylalanine diet.

PKU treatment via administration of the PAH or other enzymes has been limited by protease degradation and rapid clearance of phenylalanine metabolizing enzymes from the gastrointestinal tract. Additionally, oral BH4 loading is limited by the oxidative degradation of BH4 in the digestive tract and the potential need for compliance with a daily multiple dose regimen.

None of the methods for the treatment of HPA, in particular PKU, are entirely satisfactory. Therefore, there is a need for methods and compositions for treating HPA, and the present invention, in part, is directed to addressing this need.

SUMMARY OF THE INVENTION

The present invention relates to a composition that includes a tetrahydrobiopterin in a controlled-release pharmaceutical preparation.

The present invention also relates to a method of treating a patient with phenylyketonuria. The method includes administering, to the patient, a composition that contains tetrahydrobiopterin in a controlled-release pharmaceutical preparation.

The present invention also relates to a method of treating a patient with ADHD. The method includes administering a tetrahydropterin to the patient.

The present invention also relates to a composition for the treatment of ADHD, wherein said composition comprises a tetrahydropterin.

The present invention also relates to a pharmaceutical composition that includes (i) a tetrahydropterin; and (ii) one or more compounds selected from the group consisting of methylphenidate, clonidine, an amphetamine, and pemoline.

DETAILED DESCRIPTION OF THE INVENTION

The use of the word "a" or "an", when used in conjunction with the term "comprising" in the claims and/or the specification of the present application, may mean "one," but it is also consistent with the meaning of "one or more", "at least one", and "one or more than one".

As used herein, "treating" is meant to refer to treatment of the direct or indirect cause of a condition; to treatment of a condition's symptoms; or to both.

"Subject", as used herein, is meant to refer to any animal, such as any mammal, e.g., mice, rats, cats, rabbits, dogs, pigs, horses, cows, and primates, such as humans. Illustratively, "subject", as used herein, is meant to include human infants, human children, human adolescents, human adults, male humans, female humans, humans who are less than about 2 years of age, humans who are between about 2 years of age and 5 years of age, humans who are between about 5 and about 10 years of age, humans who are between about 10 and about 18 years of age, humans who are between about 18 and about 30 years of age, humans who are between about 30 and about 40 years of age, humans who are between about 40 and about 50 years of age, humans who are between about 50 and about 60 years of age, humans who are over about 60 years of age, humans suffering from ADHD, humans not suffering from ADHD, humans suffering from phenylketonuria, humans not suffering from phenylketonuria, humans suffering from classical phenylketonuria, humans not suffering from classical phenylketonuria, humans suffering from atypical phenylketonuria, humans not suffering from atypical phenylketonuria, humans suffering from Parkinson's Disease, humans not suffering from Parkinson's Disease, humans suffering from Alzheimer's Disease, humans not suffering from Alzheimer's Disease, humans suffering from depression, humans not suffering from depression, humans suffering from infantile autism, and/or humans not suffering from infantile autism.

One aspect of the present invention relates to compositions and methods for treating hyperphenylalaninemia (HPA). Certain embodiments include compositions comprising tetrahydrobiopterin ("BH4") in a controlled-release pharmaceutical preparation.

A controlled-release pharmaceutical preparation, according to the present invention, is one that achieves release of BH4 over an extended period of time, thereby extending the duration of therapeutic action and/or availability over that achieved by conventional delivery. An extended period of time may be from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 32, 33, 34, 35, 36, 37, 38, 39, 40, 41, 42, 43, 44, 45, 46, 47, 48 hours or more and is in contrast to immediate release formulations that typically provide most, if not all, of a therapeutic agent in minutes after being administered to a subject. There may be a variability in time release and other characteristics associated with the administration of the compositions of the invention from subject to subject, so that time release profiles, dosage amounts, and other physical characteristics may be approximations. "Controlled-release pharmaceutical preparation", as used herein, is meant to include sustained-release formulations as well as time-release formulations.

In certain embodiments, the composition may be provided in various preparations or formulations, such as a capsule, tablet, pill, matrix, depot, or gel. The amount of tetrahydrobiopterin may be provided in the approximate amounts of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, or 100 mg or more, including any intervening values or ranges therein. Tetrahydrobiopterin may be released over approximate duration of at least or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more hours. The composition may be administered by oral, injectable, depot or other route.

In some embodiments, a composition may include a number of regions, meaning 2, 3, 4, 5, 6, 7, 8, 9, 10, 15, 20, 25, 30 or more regions, that release tetrahydrobiopterin at differing rates. Such compositions may have one region that releases tetrahydrobiopterin at a higher rate, such as an immediate release region that releases a majority of therapeutic agent contained in that region upon exposure to gastrointestinal, vascular, or other body environments, as compared to a second region. Furthermore, a second region may be a controlled-released region that releases tetrahydrobiopterin for an appropriate time period, as described above.

The present invention includes methods of treating a patient with hyperphenylalaninemia by administering the compositions described herein. In certain embodiments, a patient may be administered a dosage of tetrahydrobiopterin in an approximate range 0.1, 0.2, 0.3, 0.4, 0.5, 0.6, 0.7, 0.8, 0.9, 1, 2, 3, 4, 5, 6, 7, 8, 9 mg/kg of body weight to 10, 11, 12, 13, 14, 15, 16, 17, 18, 19, 20 mg/kg of body weight.

Other objects, features, and advantages of the present invention will become apparent from the detailed description which follows. However, it should be understood that the detailed description and the specific examples presented in the "Examples" section, while indicating specific embodiments of the invention, are given by way of illustration only, since various changes and modifications within the spirit and scope of the invention will become apparent to those skilled in the art from this detailed description.

As discussed above, the present invention includes compositions and methods for treatment of HPA using controlled, sustained, and/or time release formulations that include BH4. The formulations of the invention may allow a less frequent and/or lower dose administration of therapeutic agents, thus improving compliance with and effectiveness of HPA treatment, as well as reducing side effects or toxicity.

In various instances of HPA, patients may be heterozygous for mutations in PAH: that is, they may have two distinct mutations, one in each of the two PAH alleles. Such heterozygous or "atypical" PKU patients usually have a milder form of the disease than "classic" severe cases; however these "atypical" individuals still require a phenylalanine-restricted diet and are at risk of bearing children with maternal PKU syndrome.

Typically, "atypical" PKU patients respond to BH4 therapy, and "classic" PKU patients (phenylalanine blood level>20 mg/dl) do not respond to BH4 therapy. It is estimated that 40% of PKU mutations have some residual PAH activity and would thus be candidates for BH4 therapy.

The current treatment of BH4 loading will typically be easier to comply with than a phenylalanine-restricted diet. However, BH4 pharmacokinetics, oxidative degradation of BH4 in the gastrointestinal tract, in addition to the fact that subject ingests phenylalanine several times a day, suggest that optimum cofactor delivery may require multiple doses per day. A controlled, sustained, or time-release formulation of BH4 may be advantageous, in terms of compliance to a BH4 treatment regimen. BH4 formulations useful in the practice of the present invention may contain approximately 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mg of BH4. The composition of the invention may be provided in various preparations or formulations, such as a capsule, tablet, pill, matrix, depot or gel. The compositions of the invention may release BH4 in a patient's body for a duration of at least approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more hours. The composition may be administered by a variety of routes as described herein.

In certain embodiments of the present invention, a sustained-, time-, or otherwise controlled-release formulation of BH4 can be used alone or in combination with other active ingredients for treatment of HPA and, in particular, PKU. BH4 alone or in combination with other active ingredients may be administered as a single formulation or multiple formulations with controlled, sustained, or time release kinetics that may be determined and produced by one skilled in the production of such therapeutic vehicles (for example, as described in Remington's Pharmaceutical Sciences 16th Edition, Mack Publishing Company 1980, Ed. A. Osol and Tailored Polymeric Materials for Controlled Delivery Systems, ACS Symposium Series, No. 709, Eds. McCulloch and Shalaby, which are hereby incorporated by reference).

In other embodiments of the invention, a sustained-, time-, or otherwise controlled-release formulation may include multiple regions or "compartments" in a delivery vehicle, which will allow release of a therapeutic agent(s) at different rates, such as an immediate release region combined with a controlled, sustained or time release region. The differing release rates may be incorporated into a single drug delivery vehicle or multiple drug delivery vehicles. The drug delivery vehicles may contain BH4 and other ingredients, such as protective compounds (e.g., anti-oxidants). Methods for the treatment of HPA and PKU using the sustained-, time-, or otherwise controlled-release drug delivery vehicles or formulations are contemplated.

Possible advantages of the invention include an improved compliance of patients using BH4 loading therapy and/or the reduction or elimination of a phenylalanine restricted diet. However, it is to be understood that such advantages are not to be deemed to be limitative on the scope of the present invention.

BH4, as described above, is a cofactor for PAH. In some instances, deficiencies in PAH activity may be compensated for by administration of BH4. An increase in BH4 availability may result in an increase in PAH activity that is sufficient to maintain phenylalanine blood levels within clinically acceptable ranges. BH4 is a derivative of biopterin and is a cofactor for a number of enzymes, including phenylalanine, tyrosine, and tryptophan hydroxylases. The molecule may be readily synthesized in the body. In rare cases patients cannot synthesize biopterin, which results in a variant form of HPA.

BH4 may be synthesized from guanosine triphosphate ("GTP") by the action of three different enzymes in at least four enzymatic steps (for a review see Thony et al., "Tetrahydrobiopterin Biosynthesis, Regeneration and Functions," *Biochem J.*, 347 (Part 1):1-16 (2000), which is hereby incorporated by reference). GTP cyclohydrolase I ("GTPCH"), the first enzyme in BH4 biosynthesis, catalyzes the formation of 7,8-dihydroneopterin triphosphate from GTP. The next biosynthetic step is the conversion of 7,8-dihydroneopterin triphosphate to 6-pyruvoyl-tetrahydropterin by 6-pyruvoyl-tetrahydropterin synthase ("PTPS"). It has been suggested that PTPS is the rate limiting enzyme for BH4 biosynthesis, at least in human liver. The final two-step reduction of the diketo intermediate 6-pyruvoyl-tetrahydropterin to BH4 is carried out by sepiapterin reductase ("SR"), which has been shown to be an NADPH oxidoreductase.

During the enzymatic hydroxylation of aromatic amino acids, molecular oxygen is consumed, and tetrahydrobiopterin is peroxidated and oxidized. The pterin intermediate is subsequently reduced back to BH4 by two enzymes and a reduced pyridine nucleotide (NADH) in a complex recycling reaction.

As described above, current treatment for reducing phenylalanine levels in the blood, in particular treatment of PKU, is mainly through a phenylalanine-restricted diet. Some recent reports describe the treatment of some forms of PKU by dietary administration of BH4. The present invention includes methods comprising the administration of BH4 (alone or in combination with other materials) in a time-release manner to patients diagnosed with HPA. Administration of a therapeutic agent in a time-release manner typically maintains a therapeutic level of agent for extended periods of times.

In certain embodiments of the present invention, BH4 may administered in a sustained-, time-, or otherwise controlled-release composition to provide an effective dosage of BH4 over an extended time period. Dosages of BH4 and other therapeutic agents may be in the preferred approximate range of about 2 mg/kg of body weight to approximately 20 mg/kg of body weight, and they can be continuously released for a period from about 8 hours to about 24 hours to attain therapeutically significant, substantial, effective, or efficacious levels of BH4 (e.g., levels of BH4 having an effect on activity of PAH in the targeted extracorporeal cavity, or intracorporeal cavity, compartment space, tissue, or extracellular fluid). The dosage of BH4 may vary from approximately 0.1 (preferably greater than 0.5, more preferably greater than 1, yet more preferably greater than 2, most preferably greater than 6) to 7, 8, 9, 10, 11, 12, 13, 14, 15, 16, 17, 18, 19, and 20 mg/kg of body weight. A therapeutic agent may be released over a period of time, including but not limited to approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more hours.

As will be described in more detail below, sustained release of small molecules may be improved by combining conventional pharmaceutical compositions with encapsulation, preferably with microfabricated biocapsules comprising membranes having uniformity of pore size and spacing. As will be appreciated by an artisan of ordinary skill, control of sustained diffusion of small molecules out of such a biocapsule may be obtained by controlling pore radius and surface density, and overall geometry of capsules. Sustained release of BH4 may be obtained by conventional formulation for sustained release, encapsulation or a combination thereof. The smallest pore sizes obtainable by microfabrication methods, including photolithographic, sacrificial layer methods, and combinations of these, can have a smallest dimension below about 10 nanometers, and even below about 5 nanometers as small as about 2 nanometers or on the order of a nanometer.

When encapsulation is employed to obtain sustained release of a small molecule such as the cofactor BH4, pore size and density may be employed to control diffusion kinetics in order to obtain desirable sustained release characteristics. Pore diffusion path length for particles may also be controlled by sacrificial layer methods to obtain further control of diffusion kinetics. Geometric factors, such as surface to volume ratio, may also be manipulated. Thus, embodiments of the instant invention embodied as a microfabricated capsule for sustained release of BH4 may employ a low pore density combined with small pore diameter or pore dimension(s), and long path length for BH4 particles exiting the capsule. Size of the capsule may be increased to reduce the surface to volume ratio, as appropriate for the target cavity or compartment. Thus, increased duration of sustained release and consequently duration of the time period of therapeutically efficacious levels of BH4 obtained in the target intracorporeal or extracorporeal compartment or cavity may be adjusted by increasing capsule size to decrease surface to volume ratio. An artisan of ordinary skill will comprehend that the specific target cavity, compartment or tissue will determine maximum capsule size.

Pharmaceutical compositions of the present invention comprise an effective amount of BH4 dissolved or dispersed in a pharmaceutically acceptable carrier. The pharmaceutical compositions of the present invention can contain BH4 and no other active ingredients, or it can contain BH4 and one or more other active ingredients. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains BH4 will be known to those of skill in the art in light of the present disclosure, as exemplified by Remington's Pharmaceutical Sciences, 18th Ed. Mack Printing Company, 1990, which is hereby incorporated by reference. Moreover, for animal (e.g., human) administration, it will be understood that preparations should meet sterility, pyrogenicity, general safety, and purity standards as required, for example, by FDA Office of Biological Standards.

In particular embodiments of the invention, therapeutic compositions may be provided in controlled-release (e.g., sustained-release and/or time-release) formulations. A controlled-release, (e.g., sustained-release and/or time-release) preparation according to the present invention is one that achieves slow release of a drug over an extended period of time, thereby extending the duration of drug action over that achieved by conventional delivery. Preferably such a preparation maintains a drug concentration in the blood or digestive tract within the therapeutic range for 12 hours or more. Examples of these preparations that are suitable for the incorporation of BH4 are described, for example, in Sustained Release Medications, Chemical Technology Review No. 177. Ed. J. C. Johnson. Noyes Data Corporation 1980 and Controlled Drug Delivery, Fundamentals and Applications, 2nd Edition. Eds. J. R. Robinson, V. H. L. Lee. Marcel Dekker Inc. New York 1987, which are hereby incorporated by reference. Examples of controlled-release preparations which may be suitable for incorporating BH4 (alone or in combination with one or more other active ingredients) are described in U.S. Pat. Nos. 6,355,272; 6,335,270; 6,342,250; 6,335,029; 6,326,027; 6,319,521; 6,319,520; 6,306,428; 5,676,972; and 5,102,666, which are hereby incorporated by reference.

Various formulations may include, but are not limited to enteric coated tablets or caplets, wax or polymer coated tablets or caplets or time-release matrices, or combinations thereof. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials, and combinations thereof, as would be known to one of ordinary skill in the art (see, for example, Remington's Pharmaceutical Sciences, 18th Ed. Mack Printing Company, 1990, pp. 1289-1329, which is hereby incorporated by reference). Except insofar as any conventional carrier is incompatible with the active ingredient, its use in the therapeutic or pharmaceutical compositions is contemplated.

The compositions comprising BH4 may comprise different types of carriers depending on its intended route of administration (e.g., whether it is to be administered in solid, liquid, or aerosol form and whether it needs to be sterile for such routes of administration as injection). The compositions of the present invention can be administered intravenously, intradermally, intraarterially, intramuscularly, intraperitoneally, subcutaneously, orally, by injection, by infusion, by continuous infusion, in lipid compositions (e.g., liposomes), or by other methods or any combination of the foregoing as would be known to one of ordinary skill in the art (see, for example, Remington's Pharmaceutical Sciences, 18th Ed., Mack Printing Company, 1990, which is hereby incorporated by reference). Compositions contemplated or encompassed by the instant invention include conventional pharmaceutical formulations, including those in which the matrix is soluble or insoluble in the fluids of the targeted compartment, cavity, tract or tissue, and microdevice type vehicles of agent delivery, such as silicon microfabricated capsules, or by any other method or any combination of the foregoing as would be known to one of ordinary skill in the art (see, for example, Remington's Pharmaceutical Sciences, 18th Ed., Mack Printing Company, 1990, which is hereby incorporated by reference).

The actual dosage amount of a composition of the present invention administered to a subject can be determined by physical and physiological factors such as body weight, severity of condition, the type of disease being treated, previous or concurrent therapeutic interventions, idiopathy of the patient, and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The therapeutic compositions of the present invention may be formulated into a composition in a free base, neutral, or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In certain embodiments, the therapeutic compositions of the present invention are typically prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions can be prepared by incorporating the active compound in the required amount in an appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, conventional pharmaceutical carriers such as aluminum monostearate, gelatin or combinations thereof, or microfabricated capsules comprising a diffusion control membrane, e.g., a membrane having uniform and controllable pore dimensions, pore surface density and spacing, permitting precise control of the diffusion kinetics of BH4 and other active ingredients (when present) from the capsule.

Microfabrication, in the case that a microfabricated capsule is desired, may be obtained by any method suitable, including commonly used microfabrication techniques for semiconductor manufacture, most notably, photolithographic methods of masking followed by etching of various materials including mono- and polycrystalline silicon, gallium arsenide and other crystalline semiconductor materials, glasses including Pyrex™, polymeric materials such as plastics, including by way of example, polypropylenes, polybutylenes, polyesters and polystyrenes of various densities and Teflon™. With crystalline materials, methods of employing sacrificial layers, often permit precise control of dimension by epitaxial growth achieved via molecular beam or chemical vapor deposition or the like. Such microfabrication techniques, when applied to membrane formation, permit fabrication of membranes having controllable pore size and surface density, with substantial uniformity of pore size, spacing and density, permitting precise control of diffusion kinetics. A discussion of microfabrication techniques employing a silicon substrate and sacrificial layers in combination with photolithography may be found in U.S. Pat. Nos. 6,044,981; 6,105,599; 5,938,923; which are hereby incorporated by reference.

The following references, to the extent that they provide exemplary procedural or other details supplementary to those set forth herein, are specifically incorporated herein by reference: U.S. Pat. No. 4,554,101; U.S. Pat. No. 6,057,292, U.S. Pat. No. 6,355,272; U.S. Pat. No. 6,355,270; U.S. Pat. No. 6,342,250; U.S. Pat. No. 6,335,029; U.S. Pat. No. 6,326,027; U.S. Pat. No. 6,319,521; U.S. Pat. No. 6,319,520; U.S. Pat. No. 6,306,428; U.S. Pat. No. 5,676,972; U.S. Pat. No. 5,102,666; Bird et al., 4th Meeting of the International Society for Neonatal Screening, Stockholm, Sweden, 1999; Chace et al., "Use of Phenylalanine-to-Tyrosine Ratio Determined by Tandem Mass Spectrometry to Improve Newborn Screening for Phenylketonuria of Early Discharge Specimens Collected in the First 24 Hours," *Clin. Chem.*, 44(12):2405-2409 (1998); Chen et al., "Biophysical Characterization of the Stability of the 150-Kilodalton Botulinum Toxin, the Nontoxic Component, and the 900-Kilodalton Botulinum Toxin Complex Species," *Infect. Immun.*, 66(6):2420-2425 (1998); Crameri et al., "Improved Green Fluorescent Protein by Molecular Evolution Using DNA Shuffling," *Nat. Biotechnol.*, 14(3):315-319 (1996); Crameri et al., "Molecular Evolution of an Arsenate Detoxification Pathway by DNA Shuffling," *Nat. Biotechnol.*, 15(5):436-438 (1997); Crameri et al., "DNA Shuffling of a Family of Genes from Diverse Species Accelerates Directed Evolution," *Nature*, 391(6664):288-291 (1998); Hoskins et al., "Enzymatic Control of Phenylalanine Intake in Phenylketonuria," *Lancet*, 1(8165):392-394 (1980); Kure et al., "Tetrahydrobiopterin-Responsive Phenylalanine Hydroxylase Deficiency," *J. Pediatr.*, 135(3):375-378 (1999); Remington's Pharmaceutical Sciences, 16th Ed. Mack Publishing Company, 1980; Sarkissian et al., "A Different Approach to Treatment of Phenylketonuria: Phenylalanine Degradation with Recombinant Phenylalanine Ammonia Lyase," *Proc. Natl. Acad. Sci. U.S.A.*, 96(5):2339-44 (1999); Spaapen et al., Tetrahydrobiopterin-Responsive Phenylalanine Hydroxylase Deficiency in Dutch Neonates," *J. Inherit. Metab. Dis.*, 24(3): 352-358 (2001); Trefz et al., "Successful Treatment of Phenylketonuria with Tetrahydrobiopterin," *Eur. J. Pediatr.*, 160 (5):315 (2001); Yano et al., "Directed Evolution of an Aspartate Aminotransferase with New Substrate Specificities," *Proc. Natl. Acad. Sci. U.S.A.*, 95(10):5511-5515 (1998); and Zhang et al., "Directed Evolution of a Fucosidase from a Galactosidase by DNA Shuffling and Screening," *Proc. Natl. Acad. Sci. U.S.A.*, 94(9):4504-4509 (1997).

The present invention, in another aspect thereof, relates to a method of treating a patient with ADHD. The method includes administering a tetrahydropterin to the patient.

Examples of suitable patients include subjects who are diagnosed with ADHD, as well as those who are pre-disposed to developing ADHD. The patients can be, for example, human children, human adolescents, and human adults.

"ADHD", as used herein, is meant to refer to a collection of disorders and conditions which involve attention deficit and/or hyperactivity, such as, for example, those disorders and conditions that are commonly referred to as "Attention Deficit Disorder", "Hyperactivity Disorder", "Attention Deficit Hyperactivity Disorder", and "Attention Deficit/Hyperactivity Disorder".

As used herein, "tetrahydropterin" is meant to include, for example, tetrahydrobiopterin and other tetrahydropterins that are substituted in the 6-position with a —CH(OH)—CH (OH)—CH$_3$ moiety; lipophilic tetrahydropterins; tetrahydropterins that are substituted in the 6-position with a lipophilic moiety; tetrahydropterins that are substituted in the 6-position with a substituted or unsubstituted, branched or unbranched, cyclic or non-cyclic, aliphatic or aromatic hydrocarbon, halide, oxyether, thioether, or anhydride moiety; tetrahydropterins that are substituted in the 6-position with a substituted or unsubstituted, branched or unbranched aliphatic hydrocarbon moiety; tetrahydropterins that are substituted in the 6-position with a substituted, branched aliphatic hydrocarbon moiety; tetrahydropterins that are substituted in the 6-position with an unsubstituted, branched aliphatic hydrocarbon moiety; tetrahydropterins that are substituted in the 6-position with an unsubstituted, branched aliphatic hydrocarbon moiety; tetrahydropterins that are substituted in the 6-position with an unsubstituted, unbranched aliphatic hydrocarbon moiety; tetrahydropterins that are substituted in the 6-position with an unsubstituted alkyl moiety; tetrahydropterins that are substituted in the 6-position with an unsubstituted lower alkyl moiety; tetrahydropterins that are substituted in the 6-position with an unsubstituted C1-C20 alkyl moiety; tetrahydropterins that are substituted in the 6-position with an unsubstituted C1-C20 unbranched alkyl moiety; tetrahydropterins that are substituted in the 6-position with an unsubstituted C1-C6 alkyl moiety; tetrahydropterins that are substituted in the 6-position with an unsubstituted C1-C6 unbranched alkyl moiety; and/or tetrahydropterins that are substituted in the 6-position with a dodecyl, undecyl, decyl, nonyl, octyl, heptyl, hexyl, pentyl, butyl, propyl, ethyl, or methyl group. It will be understood by those skilled in the art that the compound administered (e.g., tetrahydrobiopterin, 6-methyl-tetrahydropterin, other tetrahydropterins that are substituted in the 6-position with a substituted or unsubstituted, branched or unbranched, cyclic or non-cyclic, aliphatic or aromatic hydrocarbon, halide, oxyether, thioether, or anhydride moiety) can be cleaved and that such cleavage can occur either before or after traversing the blood brain barrier.

In one embodiment, the method of the present invention further includes administering, to the subject, a compound selected from methylphenidate, clonidine, amphetamines (e.g., methamphetamine, dextroamphetamine saccharate, dextroamphetamine sulphate, amphetamine saccharate, and amphetamine sulphate), pemoline, and combinations thereof. Where one or more of the aforementioned compounds are also administered as part of the method of the present invention, such compound or compounds can be co-administered with the tetrahydropterin, for example, as in the case where the tetrahydropterin and the compound (or compounds) are administered in a single dosage form.

As used herein, "co-administered" means that the materials are administered such that both materials are present in the subject at the same time. The materials can be administered together (e.g., as in the case where the tetrahydropterin and the compound(s) are co-administered in a single tablet or other single dosage form); the materials can be administered separately (e.g., in two separate tablets) at the same time; or they can be administered separately at different times so long as the half-life of the first-administered material is such that some (e.g., greater than about 5%, such as greater than about 10%, greater than about 15%, greater than about 20%, greater than about 25%, and/or greater than about 30%) of the first-administered material is present in the subject when the second-administered material is administered.

In another embodiment, the method of the present invention is carried out such that it does not involve co-administering methylphenidate, clonidine, an amphetamine (e.g., methamphetamine, dextroamphetamine saccharate, dextroamphetamine sulphate, amphetamine saccharate, and amphetamine sulphate), and/or pemoline.

In still another embodiment, the method of the present invention further includes administering, to the subject, a compound that mimics catecholamine and/or serotonin. Where a compound that mimics catecholamine and/or serotonin is also administered as part of the method of the present invention, such compound (or compounds) can be co-administered with the tetrahydropterin for example, as in the case where the tetrahydropterin and the compound (or compounds) that mimics catecholamine and/or serotonin are administered in a single dosage form.

In yet another embodiment, the method of the present invention is carried out such that it does not involve co-administering a compound that mimics catecholamine and/or serotonin.

In still another embodiment, the method of the present invention further includes administering, to the subject, a compound selected from the group consisting of N-acetyltyrosine, pyridoxal 5-phosphate, and combinations thereof. Where N-acetyltyrosine and/or pyridoxal 5-phosphate is also administered as part of the method of the present invention, the N-acetyltyrosine and/or pyridoxal 5-phosphate can be co-administered with the tetrahydropterin, as in the case where the tetrahydropterin and the N-acetyltyrosine and/or pyridoxal 5-phosphate are administered in a single dosage form.

In yet another embodiment, the method of the present invention is carried out such that it does not involve co-administering N-acetyltyrosine and/or pyridoxal 5-phosphate.

In still another embodiment, the method of the present invention further includes administering, to the subject, a compound selected from the group consisting of acetylcarnitine, pyridoxal 5-phosphate, and combinations thereof. Where acetylcarnitine and/or pyridoxal 5-phosphate is also administered as part of the method of the present invention, the acetylcarnitine and/or pyridoxal 5-phosphate can be co-administered with the tetrahydropterin, as in the case where the tetrahydropterin and the acetylcarnitine and/or pyridoxal 5-phosphate are administered in a single dosage form.

In yet another embodiment, the method of the present invention is carried out such that it does not involve co-administering acetylcarnitine and/or pyridoxal 5-phosphate.

In still another embodiment, the method of the present invention further includes administering, to the subject, exactly one, at least one, or more than one of the non-BH4 components of Norival. Where exactly one, at least one, or more than one of the non-BH4 components of Norival is also administered as part of the method of the present invention, such component(s) can be co-administered with the tetrahydropterin, as in the case where the tetrahydropterin and the component(s) are administered in a single dosage form.

In yet another embodiment, the method of the present invention is carried out such that it does not involve co-administering exactly one, at least one, or more than one of the non-BH4 components of Norival.

The method of the present invention can be carried out using a composition for the treatment of ADHD, to which the present invention also relates. More particularly, the present invention also relates to a composition for the treatment of ADHD, wherein the composition includes a tetrahydropterin.

In one embodiment, the composition for the treatment of ADHD includes tetrahydrobiopterin. In another embodiment, the composition for the treatment of ADHD includes a tetrahydropterin that is substituted in the 6-position with a —CH(OH)—CH(OH)—CH$_3$ moiety. In still another embodiment, the composition for the treatment of ADHD includes a lipophilic tetrahydropterin. In yet another embodiment, the composition for the treatment of ADHD includes a tetrahydropterin that is substituted in the 6-position with a lipophilic moiety. In still another embodiment, the composition for the treatment of ADHD includes a tetrahydropterin that is substituted in the 6-position with a substituted or unsubstituted, branched or unbranched, cyclic or non-cyclic, aliphatic or aromatic hydrocarbon, halide, oxyether, thioether, or anhydride moiety. In yet another embodiment, the composition for the treatment of ADHD includes a tetrahydropterin that is substituted in the 6-position with a substituted or unsubstituted, branched or unbranched aliphatic hydrocarbon moiety. In still another embodiment, the composition for the treatment of ADHD includes a tetrahydropterin that is substituted in the 6-position with a substituted, branched aliphatic hydrocarbon moiety. In yet another embodiment, the composition for the treatment of ADHD includes a tetrahydropterin that is substituted in the 6-position with an unsubstituted, branched aliphatic hydrocarbon moiety. In still another embodiment, the composition for the treatment of ADHD includes a tetrahydropterin that is substituted in the 6-position with an unsubstituted, branched aliphatic hydrocarbon moiety. In yet another embodiment, the composition for the treatment of ADHD includes a tetrahydropterin that is substituted in the 6-position with an unsubstituted, unbranched aliphatic hydrocarbon moiety. In still another embodiment, the composition for the treatment of ADHD includes a tetrahydropterin that is substituted in the 6-position with an unsubstituted alkyl moiety. In yet another embodiment, the composition for the treatment of ADHD includes a tetrahydropterin that is substituted in the 6-position with an unsubstituted lower alkyl moiety. In still another embodiment, the composition for the treatment of ADHD includes a tetrahydropterin that is substituted in the 6-position with an unsubstituted C1-C20 alkyl moiety. In yet another embodiment, the composition for the treatment of ADHD includes a tetrahydropterin that is substituted in the 6-position with an unsubstituted C1-C20 unbranched alkyl moiety. In still another embodiment, the composition for the treatment of ADHD includes a tetrahydropterin that is substituted in the 6-position with an unsubstituted C1-C6 alkyl moiety. In yet another embodiment, the composition for the treatment of ADHD includes a tetrahydropterin that is substituted in the 6-position with an unsubstituted C1-C6 unbranched alkyl moiety. In still another embodiment, the composition for the treatment of ADHD includes a tetrahydropterin that is substituted in the 6-position with a dodecyl, undecyl, decyl, nonyl, octyl, heptyl, hexyl, pentyl, butyl, propyl, ethyl, or methyl group.

The aforementioned tetrahydropterins can be administered to the patient by any conventional route. The compositions herein may be made up in any suitable form appropriate for the desired use. Examples of suitable dosage forms include oral, parenteral, or topical dosage forms.

Illustratively, suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, and the like. They may also be manufactured in the form of solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

In addition to the above, generally non-active components of the above-described formulations, these formulations can include other active materials, for example, actives which have been identified as useful in the treatment of ADHD or in the alleviation of symptoms associated therewith. Illustratively, the composition can further (i.e., in addition to one or more of the aforementioned tetrahydropterins) include a compound selected from the group consisting of methylphenidate, clonidine, an amphetamine (e.g., methamphetamine, dextroamphetamine saccharate, dextroamphetamine sulphate, amphetamine saccharate, and amphetamine sulphate), pemoline, and combinations thereof. Additionally or alternatively, the composition can be substantially free of methylphenidate, clonidine, an amphetamine (e.g., methamphetamine, dextroamphetamine saccharate, dextroamphetamine sulphate, amphetamine saccharate, and amphetamine sulphate), and/or pemoline. Still additionally or alternatively, the composition can further include a compound that mimics catecholamine and/or serotonin; or the composition can be substantially free of compounds that mimic catecholamine and/or serotonin. Still additionally or alternatively, the composition can further include N-acetyltyrosine and/or pyridoxal 5-phosphate. Still additionally or alternatively, the composition can be substantially free of N-acetyltyrosine and/or pyridoxal 5-phosphate. Still additionally or alternatively, the composition can further include acetylcarnitine and/or pyridoxal 5-phosphate. Still additionally or alternatively, the composition can be substantially free of acetylcarnitine and/or pyridoxal 5-phosphate. Still additionally or alternatively, the composition can further include exactly one, at least one, or more than one of the non-BH4 components of Norival. Still additionally or alternatively, the composition can be substantially free of exactly one, at least one, or more than one of the non-BH4 components of Norival.

As used herein, a composition is to be deemed to be "substantially free" of active component X when the concentration of active component X in the composition is below the level at which it has a measurable effect and/or when the concentration of active component X in the composition, relative to the total weight of all the actives in the composition, is less than 25% by weight (e.g., less than about 15% by weight, less than about 10% by weight, less than about 8% by weight, less than about 5% by weight, less than about 3% by weight, less than about 1% by weight, less than 15% by weight, less than 10% by weight, less than 8% by weight, less than 5% by weight, less than 3% by weight, and/or less than 1% by weight).

It will be appreciated that the actual preferred amount of tetrahydropterin (and other active components, where used) to be administered according to the present invention will vary according to the particular tetrahydropterin, the particular composition formulated, and the mode of administration. Many factors that may modify the action of the compound (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests. Suitable administration rates include, for example, from 1 mg/kg/day to 100 mg/kg/day, such as from about 1.5 mg/kg/day to about 80 mg/kg/day, from 1.5 mg/kg/day to 80 mg/kg/day, from about 2 mg/kg/day to about 60 mg/kg/day, from 1.5 mg/kg/day to 60 mg/kg/day, from about 2.5 mg/kg/day to about 40 mg/kg/day, from 2.5 mg/kg/day to 40 mg/kg/day, from about 3 mg/kg/day to about 20 mg/kg/day, from 3 mg/kg/day to 20 mg/kg/day, from about 3.5 mg/kg/day to about 10 mg/kg/day, from 3.5 mg/kg/day to 10 mg/kg/day, from about 4 mg/kg/day to about 6 mg/kg/day, from 4 mg/kg/day to 6 mg/kg/day, from about 4.5 mg/kg/day to about 5.5 mg/kg/day, from 4.5 mg/kg/day to 5.5 mg/kg/day, and/or about 5 mg/kg/day.

The present invention is further illustrated with the following examples.

EXAMPLES

Example 1

Response of PKU Patients to BH4 Therapy

PKU patients were administered a single oral dose of 10 mg/kg BH4, and blood levels of both Phe and tyrosine were monitored at 0, 4, 8, 24 hours post-dose. In this regard, it should be noted that this is half the dose administered by previous investigators. A reduction in phenylalanine level of 25% or greater, accompanied by an increase in tyrosine level of 25% or greater, within 24 hours, was considered "responding". The results are presented in Table 1.

TABLE 1

Effect of Single BH4 Dose on Phe and Tyr levels in Blood of Atypical and Classic PKU Patients

| Phenylalanine blood level (mg/dl) | Patient Type | Number of Subjects | Number of Responders | Current Treatment |
|---|---|---|---|---|
| <2 mg/dl | Normal | 0 | 0 | no therapy required |
| 2-6 mg/dl | Benign | 0 | 0 | no therapy required |
| 6-20 mg/dl | Atypical | 9 | 9 | diet required |
| 20-50 mg/dl | Classic | 6 | 0 | diet required |

Example 2

Tetrahydrobiopterin Responsive Phenylalanine Hydroxylase Deficiency in Patients with Phenylketonuria This study included 15 males and 10 females with PKU. There were 13 subjects with "classical" PKU (based on blood Phe levels greater than 20 mg/dL) and 12 with "atypical" PKU (blood Phe 6.0-20 mg/dL). The mean age of the subjects was 16.6 years with a range from 6 months to 43 years. All subjects were on a restricted Phe diet, except four subjects with atypical PKU, who had discontinued diet treatment. All of the subjects had a normal urine pterin profile and serum dihydropteridine reductase ("DHPT") activity.

Tetrahydrobiopterin (BH4) was obtained from Schircks Laboratories, Jena, Switzerland. The subjects were given BH4 10 mg/kg or 20 mg/kg by mouth after baseline blood Phe and tyrosine were drawn. Blood Phe and tyrosine were taken at 4, 8, and 24 hours and determined using tandem MS/MS (Neogen).

Fifteen subjects (60%) responded with a decline in blood phenylalanine compared to baseline levels. The mean blood Phe level prior to BH4 was 12.2 mg/dL (732 mmol/L), and, after BH4 loading, the mean level was 6.6 mg/dL (396 mmol/L) (Table 3). The mean decline in blood Phe was 53.7%. Blood tyrosine levels did not change significantly after BH4 loading (Table 4). Thirteen of the 15 subjects showed the greatest decrease in blood Phe at 24 hours. Table 2 lists the genotypes of the subjects with hyperphenylalaninemia and their response to the BH4 load. There were 13 subjects who were considered to have classical PKU, and 6 of them responded to BH4.

Ten patients did not show response to a 10 mg/kg of BH4 loading, including three individuals who had either the R261Q or Y414C allele. These mutations have been reported to respond to BH4. The patients with the R261Q allele were challenged again with 20 mg/kg BH4 and showed only a 10% drop in blood Phe level, but one subject showed a rise in blood tyrosine.

The mutations that responded to BH4 were on the catalytic, regulatory and BH4 binding domains. Five novel mutations F39L, R68S, H170D, E178G, and L308F have been identified.

TABLE 2

Response to Oral Loading of BH4 in 25 Patients with PKU

| Responsive genotypes | Non-responsive genotypes |
| --- | --- |
| I65T/R68S | IVSnt546/K371I |
| R270K/delI94 | IVS12nt1g > a/R261Q |
| R408W/F39L | G46S/unknown |
| DelI94/unknown | F299C/IVS12nt + 1g > a |
| IVS 10nt − 11g > a/E178G | Pending |
| R261Q/L308F | Y414C/IVS12nt + 1g > a |
| R408W/R68S | IVS1nt5g > t/IVS1nt5g > t |
| R408/R68S | IVS12nt + 1g > a/E280K |
| R241C/V388M | IVS12nt + 1g > a/P281L |
| P407S/R408W | R408W/R261Q |
| F39L/F55fsdelT | |
| F39L/F55fsdelT | |
| IVS1nt5g > a/H170D | |
| Y414C/R408W | |
| E390G/IVS12nt1 | |

*60% responded to BH4

TABLE 3

Positive Blood Phe Response to BH4 in Patients with PKU

| | Zero Time | 24 Hour |
| --- | --- | --- |
| P407S/R408W | 504 | 276 |
| I65T/T68S | 1110 | 852 |
| R270K/delI94 | 1224 | 672 |
| Y414C/? | 792 | 534 |
| R408W/F39L | 1008 | 612 |
| DelI94/? | 1530 | 816 |
| IVS1nt5g > a/H170D | 510 | 162 |
| E390G/IVS12nt1g > a | 624 | 186 |
| IVS10nt11g > a/E178G | 576 | 312 |
| R408W/R68S | 282 | 114 |
| R408W/R68S | 870 | 516 |
| R261Q/L308F | 342 | 96 |
| F39L/F55fsdelT | 948 | 606 |
| F39L/F55fsdelT | 468 | 132 |
| R241C/V388M | 186 | 96 |
| R408W/R261Q | 900 | 744 |

TABLE 4

Blood Tyrosine in PKU Patients with Response to BH4

| | Zero Time | 24 Hour |
| --- | --- | --- |
| P407S/R408W | 61 | 55 |
| I65T/T68S | 42 | 104 |
| R270K/delI94 | 48 | 69 |
| Y414C/? | 60 | 66 |
| R408W/F39L | 23 | 51 |
| DelI94/? | 73 | 126 |
| IVS1nt5g > a/H170D | 79 | 121 |
| E390G/IVS12nt1g > a | | |
| IVS10nt11g > a/E178G | 50 | 54 |
| R408W/R68S | 33 | 51 |
| R408W/R68S | 42 | 60 |
| R261Q/L308F | 33 | 38 |
| F39L/F55fsdelT | 44 | 60 |
| F39L/F55fsdelT | 25 | 72 |
| R241C/V388M | 66 | 57 |
| R408W/R261Q | 45 | 23 |

Example 3

Investigation into the CNS Effects of BH4 and 6-Methyl BH4

To comparatively investigate the CNS effects of BH4 and methyl BH4, we used mice both with and without PKU. A single dose of either compound was given IM, 100 mg/kg to PKU afflicted and normal mice, with control groups receiving buffer only. After 1 hr, a time sufficient to observe changes in brain chemistry, the mice were sacrificed, and brains were sent out for analysis of 3-O-methyldopa ("3OMD"), 5-hydroxytryptamine ("15HT") (serotonin), dihydroxybenzoic acid ("DHBA"), dopamine ("DA"), dihydroxyphenylacetic acid ("DOPAC"), hydroxyindoleacetic acid ("HIAA"), homovanilic acid ("HVA"), and methoxyhydroxyphenylglycol ("MPHG") levels.

The data, summarized in Table 5 and in Table 6, establish that both compounds can enter the brain, causing levels of catecholamines and serotonin to increase. Even the PKU mouse the brain levels of these metabolites normalizes. These data indicate that, overall, a greater effect on CNS chemistry is obtained from administration of 6-methyl BH4, evidencing a better ability to traverse the blood brain barrier for 6-methyl BH4 as compared to BH4. The preceding supports the conclusion that current pharmaco-therapies for ADHD can be replaced by BH4 and other tetrahydropterins.

TABLE 5

Levels of Metabolites in Mouse Brain Following BH4 and 6-Methyl BH4 Treatment

| Animal | No. | Levels in nmol/g wet weight | | | | | | | |
|---|---|---|---|---|---|---|---|---|---|
| | | 3OMD | 5HT | DHBA | DA | DOPAC | HIAA | HVA | MPHG |
| Non PKU control | 640 | 0.67 | 0.91 | 818.2 | 7.84 | 0.50 | 2.83 | 0.87 | 0.26 |
| | 619 | 0.61 | 0.88 | 799.6 | 9.97 | 0.56 | 3.16 | 0.93 | 0.27 |
| | 508 | 0.51 | 1.12 | 762.9 | 10.40 | 0.66 | 3.56 | 0.92 | 0.27 |
| | 596F | 0.42 | 1.02 | 758.7 | 10.73 | 0.67 | 3.26 | 0.88 | 0.25 |
| PKU control | 463 | 0.35 | 0.19 | 787.7 | 7.80 | 0.36 | 1.58 | 0.64 | 0.11 |
| | 624F | 0.19 | 0.15 | 772.2 | 6.57 | 0.31 | 1.00 | 0.62 | 0.11 |
| | 636 | 0.44 | 0.17 | 777.4 | 5.14 | 0.30 | 0.97 | 0.68 | 0.17 |
| | 628 | 0.47 | 0.17 | 735.7 | 6.58 | 0.46 | 0.93 | 0.94 | 0.13 |
| PKU BH4 | 627 | 0.48 | 0.16 | 776.4 | 6.28 | 0.40 | 0.91 | 0.80 | 0.18 |
| | 545 | 0.16 | 0.23 | 759.0 | 9.48 | 0.53 | 1.68 | 1.04 | 0.21 |
| | 631F | 0.09 | 0.15 | 755.5 | 6.91 | 0.51 | 0.94 | 0.77 | 0.26 |
| | 603 | 0.55 | 0.24 | 741.9 | 8.08 | 0.37 | 1.45 | 0.94 | 0.16 |
| PKU 6-Me BH4 | 590 | 0.39 | 0.20 | 764.7 | 10.16 | 0.51 | 1.70 | 1.18 | 0.36 |
| | 626 | 0.26 | 0.15 | 774.3 | 7.14 | 0.40 | 1.03 | 0.94 | 0.26 |
| | 553 | 0.17 | 0.28 | 758.6 | 6.46 | 0.52 | 1.64 | 0.92 | 0.32 |
| | 587F | 0.47 | 0.24 | 756.1 | 7.27 | 0.48 | 1.41 | 0.91 | 0.18 |
| Non PKU BH4 | 620 | 0.58 | 1.27 | 774.2 | 9.06 | 0.68 | 3.49 | 1.08 | 0.36 |
| | 632F | 0.27 | 1.21 | 766.5 | 9.56 | 0.62 | 3.23 | 1.09 | 0.30 |
| | 630 | 0.60 | 1.16 | 734.9 | 9.63 | 0.72 | 3.19 | 1.22 | 0.40 |
| | 507 | 0.41 | 1.53 | 750.5 | 9.93 | 0.79 | 3.58 | 1.18 | 0.33 |
| Non PKU 6-Me BH4 | 622 | 0.57 | 1.07 | 775.7 | 10.86 | 0.61 | 3.09 | 1.26 | 0.31 |
| | 588F | 0.29 | 1.31 | 762.3 | 10.26 | 0.65 | 3.56 | 0.99 | 0.26 |
| | 556 | 0.36 | 1.21 | 760.0 | 11.50 | 0.66 | 3.65 | 1.20 | 0.30 |
| | 621 | 0.44 | 1.11 | 775.0 | 10.56 | 0.59 | 3.22 | 1.28 | 0.29 |

TABLE 6

Levels of Metabolites in Mouse Brain Following BH4 and 6-Methyl BH4 Treatment

| Animal | No. | Levels in nmol/l | | | | | | | |
|---|---|---|---|---|---|---|---|---|---|
| | | 3OMD | 5HT | DHBA | DA | DOPAC | HIAA | HVA | MPHG |
| Non PKU control | 640 | 134.2 | 181.9 | 818.2 | 1567.4 | 99.4 | 566.4 | 174.2 | 51.7 |
| | 619 | 122.4 | 175.1 | 799.6 | 1993.8 | 111.7 | 632.8 | 186.3 | 53.2 |
| | 508 | 101.6 | 223.3 | 762.9 | 2080.4 | 132.9 | 711.7 | 184.0 | 54.2 |
| | 596F | 84.8 | 204.3 | 758.7 | 2146.1 | 134.4 | 652.6 | 175.5 | 50.6 |
| PKU control | 624F | 38.5 | 29.5 | 772.2 | 1313.7 | 61.9 | 199.5 | 123.6 | 21.0 |
| | 628 | 94.3 | 33.3 | 735.7 | 1315.1 | 91.0 | 186.3 | 187.3 | 25.4 |
| | 636 | 88.7 | 33.5 | 777.4 | 1027.5 | 59.8 | 194.0 | 136.3 | 34.3 |
| | 463 | 69.9 | 37.9 | 787.7 | 1560.3 | 71.7 | 315.5 | 127.1 | 22.0 |
| PKU BH4 | 627 | 95.1 | 31.5 | 776.4 | 1256.0 | 80.9 | 181.1 | 160.6 | 35.2 |
| | 545 | 32.9 | 45.7 | 759.0 | 1896.3 | 105.7 | 336.9 | 207.0 | 42.9 |
| | 631F | 18.2 | 30.4 | 755.5 | 1382.2 | 101.0 | 188.0 | 153.6 | 51.6 |
| | 603 | 110.4 | 48.3 | 741.9 | 1616.2 | 73.1 | 290.6 | 188.7 | 31.6 |
| PKU 6-Me BH4 | 590 | 77.7 | 40.0 | 764.7 | 2031.2 | 101.7 | 340.4 | 236.9 | 71.2 |
| | 626 | 51.9 | 30.0 | 774.3 | 1427.4 | 80.6 | 205.6 | 187.2 | 52.1 |
| | 553 | 34.9 | 56.7 | 758.6 | 1292.6 | 104.5 | 328.1 | 184.5 | 63.2 |
| | 587F | 94.1 | 47.6 | 756.1 | 1454.4 | 95.6 | 282.2 | 182.1 | 36.3 |
| Non PKU BH4 | 620 | 115.6 | 253.5 | 774.2 | 1811.4 | 136.6 | 697.5 | 216.9 | 72.5 |
| | 632F | 53.3 | 242.3 | 766.5 | 1912.5 | 124.4 | 646.1 | 217.7 | 60.6 |
| | 630 | 119.7 | 231.2 | 734.9 | 1926.7 | 143.4 | 638.7 | 243.0 | 80.2 |
| | 507 | 81.1 | 305.2 | 750.5 | 1985.9 | 158.6 | 716.9 | 236.6 | 66.7 |
| Non PKU 6-Me BH4 | 622 | 114.5 | 214.3 | 775.7 | 2172.4 | 121.6 | 617.3 | 252.9 | 62.9 |
| | 621 | 87.7 | 222.6 | 775.0 | 2112.1 | 118.9 | 643.9 | 256.9 | 58.9 |
| | 588F | 58.2 | 261.1 | 762.3 | 2051.2 | 129.6 | 712.0 | 197.1 | 51.2 |
| | 556 | 71.7 | 242.3 | 760.0 | 2300.5 | 132.5 | 730.5 | 240.6 | 59.7 |

Example 4

Effect of BH4 on Human with ADHD

BH4 was given to one male human patient, 16 years of age, suffering from ADHD. The patient was given mg/kg per day as a single dose every morning for 1 week. The parents were asked to evaluate the following parameters: behavior, attentiveness concentration, and forgetfulness. The parents and the patient indicated that, with regard to all parameters, the patient was better after receiving BH4 treatment. Prior to receiving BH4 treatment, the patient was given a Connors' Continuous Performance Test—2nd edition ("CPT2"), which is an objective, computerized test that is commonly used to identify attention problems and measure treatment effectiveness. At the end of the BH4 trial, the patient again took the CPT2. The patient's score on the second CPT2 was greatly improved relative to the first CPT2.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. A method of treating a patient with attention deficit hyperactivity disorder (ADHD), said method comprising administering a tetrahydropterin to a patient in need thereof.

2. A method according to claim 1, further comprising: administering a compound selected from the group consisting of methylphenidate, clonidine, an amphetamine, pemoline, and combinations thereof.

3. A method according to claim 2, wherein the tetrahydropterin and the compound are co-administered.

4. A method according to claim 2, wherein the tetrahydropterin and the compound are co-administered in a single dosage form.

5. A method according to claim 1, wherein said method does not involve coadministering methylphenidate, clonidine, an amphetamine, and/or pemoline.

6. A method according to claim 1, further comprising: administering a compound that mimics catecholamine and/or serotonin.

7. A method according to claim 6, wherein the tetrahydropterin and the compound are co-administered.

8. A method according to claim 6, wherein the tetrahydropterin and the compound are co-administered in a single dosage form.

9. A method according to claim 1, wherein said method does not involve coadministering a compound that mimics catecholamine and/or serotonin.

10. A method according to claim 1, further comprising: administering a compound selected from the group consisting of N-acetyltyrosine, pyridoxal 5-phosphate, and combinations thereof.

11. A method according to claim 10, wherein the tetrahydropterin and the compound are co-administered.

12. A method according to claim 10, wherein the tetrahydropterin and the compound are co-administered in a single dosage form.

13. A method according to claim 1, wherein said method does not involve coadministering N-acetyltyrosine and/or pyridoxal 5-phosphate.

14. A method according to claim 1, further comprising: administering a compound selected from the group consisting of acetylcarnitine, pyridoxal 5-phosphate, and combinations thereof.

15. A method according to claim 14, wherein the tetrahydropterin and the compound are co-administered.

16. A method according to claim 14, wherein the tetrahydropterin and the compound are co-administered in a single dosage form.

17. A method according to claim 1, wherein said method does not involve coadministering acetylcarnitine and/or pyridoxal 5-phosphate.

18. A method according to claim 1, wherein the tetrahydropterin is a tetrahydropterin substituted in the 6-position with a —CH(OH)—CH(OH)—CH$_3$—, moiety.

19. A method according to claim 1, wherein the tetrahydropterin is tetrahydrobiopterin.

20. A method according to claim 1, wherein the tetrahydropterin is a tetrahydropterin substituted in the 6-position with a substituted or unsubstituted, branched or unbranched, cyclic or non-cyclic, aliphatic or aromatic hydrocarbon, halide, oxyether, thioether, or anhydride moiety.

21. A method according to claim 1, wherein the tetrahydropterin is a tetrahydropterin substituted in the 6-position with a substituted or unsubstituted, branched or unbranched aliphatic hydrocarbon moiety.

22. A method according to claim 1, wherein the tetrahydropterin is a tetrahydropterin substituted in the 6-position with a methyl group.

* * * * *